US009067864B2

(12) United States Patent
Sommer et al.

(10) Patent No.: US 9,067,864 B2
(45) Date of Patent: Jun. 30, 2015

(54) PROCESS FOR PRODUCING AROMATIC AMINES

(75) Inventors: Knut Sommer, Krefeld (DE); Ido Schwarz, Düsseldorf (DE); Susanne Buchholz, Köln (DE); Franz-Ulrich Von Gehlen, Krefeld (DE); Andre Lago, Minghang District (CN); Karl-Heinz Wilke, Moers (DE); Holger Orzesek, Gelsenkirchen-Buer (DE); Hans-Georg Pirkl, Leverkusen (DE); Peter Lehner, Ratingen (DE); Stephan Schubert, Leverkusen (DE)

(73) Assignee: Bayer MaterialScience AG, Leverkusen (DE)

( * ) Notice: Subject to any disclaimer, the term of this patent is extended or adjusted under 35 U.S.C. 154(b) by 1991 days.

(21) Appl. No.: 11/881,014

(22) Filed: Jul. 25, 2007

(65) Prior Publication Data

US 2008/0234518 A1 Sep. 25, 2008

(30) Foreign Application Priority Data

Jul. 29, 2006 (DE) ........................ 10 2006 035 203

(51) Int. Cl.
*C07C 209/00* (2006.01)
*C07C 209/36* (2006.01)

(52) U.S. Cl.
CPC .................................. *C07C 209/36* (2013.01)

(58) Field of Classification Search
None
See application file for complete search history.

(56) References Cited

U.S. PATENT DOCUMENTS

| | | | | |
|---|---|---|---|---|
| 3,136,818 | A | 6/1964 | Sperber et al. | 260/580 |
| 3,636,152 | A | 1/1972 | Szigeth | 260/580 |
| 3,871,445 | A | 3/1975 | Wanka et al. | 165/107 |
| 3,882,048 | A | 5/1975 | Thelen et al. | 252/464 |
| 4,265,834 | A | 5/1981 | Birkenstock et al. | 564/421 |
| 4,740,621 | A | 4/1988 | Adams et al. | 564/419 |
| 5,304,525 | A | 4/1994 | Immel et al. | 502/185 |
| 5,679,858 | A | 10/1997 | Langer et al. | 564/423 |
| 5,808,157 | A | 9/1998 | Langer et al. | 564/422 |
| 5,877,350 | A | 3/1999 | Langer et al. | 564/423 |
| 5,962,365 | A | 10/1999 | Langer et al. | 502/180 |

FOREIGN PATENT DOCUMENTS

| | | |
|---|---|---|
| CA | 2178700 | 12/1996 |
| GB | 1 452 466 | 10/1976 |

*Primary Examiner* — Clinton Brooks

(74) *Attorney, Agent, or Firm* — Donald R. Palladino; Lyndanne M. Whalen

(57) ABSTRACT

Aromatic amines are produced by adiabatic hydrogenation of nitroaromatic compounds in the gas phase on one or more fixed catalysts. The nitroaromatic reactant is passed over the catalyst under pressure and at elevated temperature with hydrogen, water, optionally nitrogen and substantially in the absence of the aromatic amine produced from the nitroaromatic.

10 Claims, No Drawings

PROCESS FOR PRODUCING AROMATIC AMINES

BACKGROUND OF THE INVENTION

The invention relates to a process for the adiabatic hydrogenation of nitroaromatic compounds nitroarenes to form aromatic amines in the gas phase on fixed catalysts. In this process, the nitroaromatic reactant is passed over the catalyst under pressure and at elevated temperature with hydrogen, water, optionally nitrogen and substantially in the absence of the aromatic amine produced from the nitroaromatic reactant.

Aromatic amines are important intermediates which have to be available at low cost and in large quantities. For that reason, plants for the hydrogenation of nitrobenzene, for example, have to be constructed with very large capacities.

The hydrogenation of nitroaromatic compounds is a highly exothermic reaction. Thus, for example, at 200° C., the hydrogenation of nitroxylene to form xylidene releases approx. 488 kJ $mol^{-1}$. The hydrogenation of nitrobenzene to form aniline releases approx. 544 kJ $mol^{-1}$. From both an ecological and an economic perspective, the dissipation and use of the heat of reaction is an important element in the performance of processes for hydrogenating nitroaromatic compounds.

Thus in an established processing mode the catalyst is operated as a fluidized, heat-stabilized bed (U.S. Pat. No. 3,136,818). This processing mode results in effective heat dissipation but it suffers from a non-uniform residence time distribution (nitrobenzene leakage) and catalyst abrasion.

Narrow residence time distributions and low catalyst abrasion are achievable in principle in reactors having a static catalyst bed. However, problems with the temperature control of the catalyst beds frequently occur in such reactors. As a general rule, temperature-controlled multitube fixed-bed reactors are used ("isothermal operation") which, particularly in the case of large reactors, have a very elaborate cooling circuit (DE-OS 2 201 528). Such reactors are complex and give rise to high investment costs, since the manufacture of a reactor made up of many thousands of individual tubes is very complicated and can only be performed by specialist companies at high cost. In addition, the size of the plant leads to rapidly growing problems in terms of mechanical strength and uniform temperature control of the catalyst bed which make the construction of large units of this type impracticable from a purely technical viewpoint too. Therefore, the use of this principle to construct modern plants on a world scale, which require production capacities of many hundreds of thousands of tonnes per year, is entirely unrealistic.

In contrast, simple reactors such as those suitable for conducting the process of the present invention described herein contain only catalyst beds on or between simple support grates and/or metal screens and have no system for heat balancing in the reactor. In other words, the need for complex measures to control the temperature of the catalyst beds, through the use of heat transfer oil, for example, is entirely eliminated. In this type of reactor the reaction enthalpy is reflected quantitatively in the temperature difference between the reactant and product gas stream ("adiabatic operation"). Reactors of this type are easy to transfer from a pilot-plant scale (mini-plant) to the scale of a large production plant, which considerably simplifies process development. The latter involves, for example, the fine tuning of operating parameters such as pressure, temperature, rate of flow of the reaction gases, concentration of co-reactants, etc., as well as other factors such as choice of catalyst. All of these factors must be optimized in order to achieve the greatest possible yield and selectivity. The possibility of being able to optimize these many variables in a relatively small laboratory scale test plant and then transfer the results without difficulty to a large production plant offers considerable advantages, since, for example, there is no need in principle for a pilot phase and the construction of a plant with the necessary production capacity can begin immediately. Furthermore, reactors of this type are inexpensive and robust in all sizes.

GB 1,452,466 discloses a process for hydrogenating nitrobenzene in which an adiabatic reactor is connected in series to an isothermal reactor. The majority of the nitrobenzene is reacted in a temperature-controlled multitube fixed-bed reactor. Only the hydrogenation of the residual content of nitrobenzene takes place with a relatively low hydrogen excess (less than 30:1) in an adiabatic reactor. However, the complete elimination of a temperature-controlled reactor with a purely adiabatic reaction and the associated advantages is not taught in GB 1,452,466.

DE-AS 1 809 711 teaches uniform introduction of liquid nitro compounds into a hot gas stream by atomization, preferably at constricted points directly in front of the reactor. The design of the reactor is not mentioned in DE-AS 1 809 711. It follows from the example, however, that in spite of a considerable hydrogen excess, at least 34% of the reaction enthalpy does not leave the reactor with the product gas, so the reactor is not operated adiabatically.

DE-OS 3 636 984 describes a process for the coupled production of nitro- and dinitroaromatics from the corresponding hydrocarbons by nitration and subsequent hydrogenation. Hydrogenation takes place in the gas phase at temperatures between 176 and 343.5° C. An apparatus for gas-phase hydrogenation is described which is composed substantially of two reactors connected in series with intermediate cooling and intermediate introduction of the reactant, but no mention is made of their size and design. However, it follows from the temperature profile of the reactors that a considerable proportion of the heat of reaction does not leave the reactor with the product gas stream. Thus reactor 1 has an inlet temperature of 181.7° C., a hottest point of 315.6° C. and an outlet temperature of 277.2° C.; and reactor 2 has an inlet temperature of 203.9° C., a hottest point of 300° C. and an outlet temperature of 296.7° C. No mention is made in DE-OS 36 36 984 of a cooling system for the reactors for industrial reactions of, e.g., 80,000 tonnes per year. Neither DE-OS 36 36 984 nor DE-OS 18 09 711 deals explicitly with the problem of heat dissipation in gas-phase hydrogenation reactions.

In all of the aforementioned publications, copper catalysts are used. These copper catalysts are operated exclusively with low loads (<0.1 $g_{nitroarene}/[ml_{catalyst}\cdot h]$) and at a low temperature level. This results in low space-time yields.

In addition to the aforementioned copper catalysts, numerous other contacts are described as suitable for the gas-phase hydrogenation of nitroarenes. They are described in many publications and include as active hydrogenation elements Pd, Pt, Ru, Fe, Co, Ni, Mn, Re, Cr, Mo, V, Pb, Ti, Sn, Dy, Zn, Cd, Ba, Cu, Ag, Au, and their compounds, in part as oxides, sulfides or selenides and also in the form of a Raney alloy and on supports, such as $Al_2O_3$, $Fe_2O_3/Al_2O_3$, $SiO_2$, silicates, carbon, $TiO_2$, $Cr_2O_3$. These catalysts too are operated only with low loads in a temperature range below 350° C.

DE-A 2 244 401 and DE-A 2 849 002 describe palladium catalysts on aluminum oxide supports which are operated as static catalyst beds in heat-exchanger tubes under normal pressure with loads of less than 1 $g_{nitroarenes}/[ml_{catalyst}\cdot h]$ and low hydrogen/nitrobenzene ratios.

DE-A 4 039 026 describes palladium catalysts on graphite supports which are operated under similar conditions to the palladium catalysts on aluminum oxide. In all of these process variants, the large amount of heat that is generated from the reaction has to be removed from an industrial reactor by means of a complex heat exchanger system.

Only the patents EP 0 696 573 B1, EP 0 696 574 B1, EP 0 748 789 B1 and EP 0 748 790 B1 are directed to processes performed under purely adiabatic conditions. EP 0696574 B1 describes in very general terms the process for producing aromatic amines in which a gas mixture made up of nitroaromatic compounds and hydrogen is passed through the catalyst under adiabatic conditions. In the processes disclosed in EP 0 696 573 B1, EP 0 748 789 B1 and EP 0 748 790 B1, certain advantages are obtained in each case by altering various parameters.

EP 0 696 573 B1 teaches that the advantage of particularly high selectivities is achieved if the nitroaromatic reactant is passed over the catalyst with, in addition to hydrogen, a multiple of the aromatic amine produced in the reaction and a multiple of water. In this mode of operation, each catalyst volume contains at least 2 moles of amino groups and 4 moles of water per mole of nitro group. The catalysts described are the same as in EP 0 696 574 B1. The disadvantage of this processing mode is that large amounts of compounds which in principle are dispensable for the actual reaction, namely water and amine, have to be continually recycled. In particular, the constant recycling of at least 2 equivalents of the amine that is formed, in other words the valuable product of the process, is extremely disadvantageous because the amine that is produced is repeatedly exposed to high temperatures.

Patents EP 0 748 789 B1 and EP 0 748 790 B1 describe advantages obtained only through the use of specialized catalyst systems:

Palladium catalysts on graphite or graphite-containing coke with a palladium content of >1.5 and <7 mass % are disclosed in EP 0 748 789 B1. The advantage attributed to these catalysts is due to exceptionally long cycle times in comparison to all previously described catalysts. The disadvantage of this process is the immensely high catalyst cost that is inevitably associated with the high palladium concentrations. The patent does not indicate that the high catalyst costs arising from the large amounts of palladium needed for an industrial application can be offset by the long cycle times.

Palladium-lead catalysts on graphite or graphite-containing coke with a palladium content of 0.001 to 7 mass % are disclosed in EP 0748 790 B1. The advantage attributed to these catalysts is higher selectivity in comparison to analogous catalysts without the addition of lead. All of the examples described in this patent used catalysts with 2 mass % of palladium, so the disadvantage of high catalyst costs applies in this case too.

Hydrogenation in the presence of water is not taught in either EP 0 748 789 B1 or EP 0 748 790 B1.

SUMMARY OF THE INVENTION

The object of the present invention was therefore to provide a process for producing aromatic amines which includes the particular advantages of the processes disclosed in EP 0 696 573 B1, EP 0 748 789 B1 and EP 0 748 790 B1 (i.e., long cycle times, high selectivities) without their disadvantages (i.e., constant recycling of large amounts of valuable amine, large amount of water to be introduced, high catalyst costs).

Surprisingly it has been found that this objective is achieved if the nitroaromatic reactant is passed over the catalyst under pressure and at elevated temperature with hydrogen, water, optionally nitrogen and substantially in the absence of the aromatic amine produced from the nitroaromatic reactant. This processing mode leads in a simple manner to long cycle times and high selectivities combined with decisively improved economic efficiency, since none or optionally only minimal amounts of the aromatic amine that is produced are recycled. Moreover, in preferred embodiments, there is no need to introduce large amounts of water and inexpensive, catalysts with precious metal contents lower than previously employed can be used.

DETAILED DESCRIPTION OF THE INVENTION

The present invention relates to a process for producing aromatic amines corresponding to the formula:

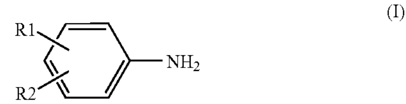

(I)

in which $R^1$ represents hydrogen, a methyl group, an ethyl group, or an amino group, and $R^2$ represents hydrogen, a methyl group or an ethyl group, by hydrogenating a nitroaromatic compound corresponding to the formula

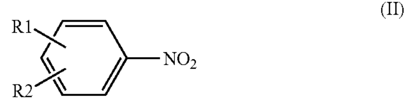

(II)

in which $R^2$ represents hydrogen, a methyl group or an ethyl group, and $R^3$ represents hydrogen, a methyl group, an ethyl group or a nitro group, in the gas phase with hydrogen on a fixed catalyst.

In this process, hydrogenation is conducted at an absolute pressure of from 1 to 50 bar, preferably from 2 to 20 bar, most preferably from 2 to 10 bar and at an inlet temperature of the gas mixture used of from 150 to 400° C., preferably from 200 to 300° C., most preferably from 220 to 280° C. and a maximum catalyst temperature of 600° C., preferably 550° C., most preferably 500° C., under adiabatic conditions. A gas mixture is passed through the fixed catalyst(s) at the start of hydrogenation. This gas mixture includes from 3 to 150 moles, preferably from 6 to 125 moles, more preferably from 12 to 100 moles, most preferably from 50 to 90 moles of hydrogen per mole of nitro groups, and from 1 to 100 moles, preferably from 3 to 50 moles, more preferably from 4 to 25 moles of water per mole of nitro groups. Hydrogen is separated off from the reaction mixture obtained during hydrogenation and the hydrogen, which is substantially free from the aromatic amine, is returned to the hydrogenation.

The gas mixture is preferably homogenized on the fixed catalyst(s) before the start of hydrogenation, i.e. mixed in a static mixer, for example.

The fixed catalysts are preferably arranged in the reactor in the form of catalyst beds, for example as a fixed catalyst bed. Monolithic reactors whose walls are coated with catalytically active metals are also suitable for conducting the process of the present invention.

The fixed catalysts can be arranged in one reactor or in multiple reactors connected in series. A parallel operation of multiple reactors is also possible. In the case of multiple reactors or catalyst beds or monoliths connected in series, the fresh gas mixture is preferably passed through only the first of the reactors. The gas mixture obtained from the first reactor, optionally replenished with fresh hydrogen and fresh nitroaromatic compound, is then passed through the next reactor. The removal of individual components or the addition of other or further components is also possible between the reactors, however.

The process of the present invention is performed continuously. At the start of hydrogenation (the start of hydrogenation means the point of entry of the gas mixture into the hydrogenation reactor in continuous operation), a gas mixture is passed through the fixed catalyst(s) which per mole of nitro groups contains from 3 to 150 moles of hydrogen and from 1 to 100 moles of water. This means that this gas mixture is passed continuously through the reactor containing the fixed catalysts. If the hydrogenation is performed in multiple reactors connected in series, this gas mixture is passed continuously through the first of the reactors in the direction of flow.

If in the case of multiple reactors connected in series, the aromatic amine is separated off by condensation not only after the last reactor but after each reactor, this gas mixture is preferably passed through each of the reactors.

In a preferred embodiment of the present invention, up to 50% of the hydrogen contained in the gas mixture before the start of hydrogenation is replaced by an inert gas, preferably nitrogen. Then the gas mixture contains: (a) from 3 to 150 moles, preferably from 6 to 125 moles, more preferably from 12 to 100 moles, most preferably from 50 to 90 moles of hydrogen per mole of nitro groups; (b) from 0 to 75 moles, preferably from 0.1 to 62.5 moles, more preferably from 0.5 to 50 moles and most preferably from 2 to 45 moles of inert gas per mole of nitro groups; and (c) from 1 to 100 moles, preferably from 3 to 50 moles, more preferably from 4 to 25 moles of water per mole of nitro groups. This leads to a further rise in the already high selectivities with which the aromatic amines are formed in the process of the present invention. Due to lower proportions of by-products, the high selectivities allow a less complex processing of the aromatic amines that are formed in comparison to the isothermal operation described in the prior art.

The hydrogen is preferably separated off from the reaction mixture leaving the reactor or leaving the last reactor in the direction of flow in the case of multiple reactors connected in series or leaving each reactor in the case of multiple reactors connected in parallel by separating off at least a part of the condensable components of the reaction mixture, preferably by condensation. Then hydrogen and optionally also inert gas (nitrogen) and optionally water vapor are returned to the reactor or to the first of a series of reactors or to each of multiple reactors connected in parallel.

Preferred nitroarenes for the process of the invention are those corresponding to the formula

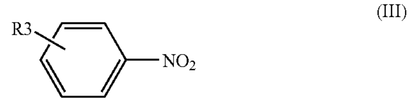

(III)

in which $R^3$ has the meaning given above.

Nitrobenzene is particularly preferred as the nitroaromatic reactant. Nitrobenzene can be prepared in various ways. It is preferably prepared by the mononitration of benzene, most preferably under adiabatic conditions as described in EP-A-708 076. EP-A-708 076 discloses a process for the adiabatic dinitration of aromatic compounds such as benzene for example. EP-A-708 076 discloses typical reaction conditions such as the temperature in the reactor inlet, the dispersion conditions (dispersion energy to be introduced for the first dispersion and the redispersion and the suitable dispersing elements), and the residence time between the dispersion stages both for the first nitration stage (to nitrobenzene) and for the subsequent second nitration stage (to dinitrobenzene). Apart from the stoichiometric excess of nitrating acid or nitric acid in relation to the aromatic compound which is necessary for dinitration, the teaching from EP-A-708 076 is also applicable to the mononitration of benzene.

A production plant that is suitable for conducting the process of the present invention preferably contains at least one adiabatic reactor with a static catalyst. Preferably, a maximum of 10, more preferably a maximum of 5, most preferably a maximum of 3 such reactors are arranged in series. Each of the reactors connected in series can be replaced by multiple reactors connected in parallel. Preferably a maximum of 5, more preferably a maximum of 3, most preferably a maximum of 2 reactors are connected in parallel. The process of the present invention may therefore be conducted in a maximum of 50 reactors and a minimum of one reactor.

Multiple reactors with one catalyst bed can also be replaced by a smaller number of reactors with multiple catalyst beds.

The reactors are preferably simple vessels with isolated catalyst beds, as described, for example, in Ullmann's Encyclopedia of Industrial Chemistry (fifth, completely revised edition, vol. B4, page 95-102 and page 210-216).

The catalyst beds are preferably arranged in known manner on or between gas-permeable walls. Metallic support grates and/or metal screens are preferably used for this purpose.

In the case of thin beds, in particular, technical devices to achieve a uniform gas distribution can also be added above, below or above and below the catalyst bed. These can be, for example, perforated plates, bubble trays, valve trays or other inserts which bring about a uniform introduction of the gas into the catalyst bed by generating a small but uniform pressure loss.

The thickness of the catalyst bed(s) can be between 1 cm and 5 m, preferably between 5 cm and 2 m, more preferably between 10 cm and 1 m, most preferably between 30 cm and 60 cm.

All contacts previously described for the gas-phase hydrogenation of nitro compounds can be used as catalysts. These contain the aforementioned elements either as an alloy or as mixed oxides and optionally on an inert support. Particularly suitable supports are: $\alpha$- and $\gamma$-$Al_2O_3$, $SiO_2$, $TiO_2$, terra rossa and limonite, $Fe_2O_3/Al_2O_3$ mixtures, $CuO/Cr_2O_3$ mixtures, water glass, graphites, cokes, carbon nanotubes and carbon fibers. However, other supports can also be used in principle.

The catalysts described in DE-OS 2 849 002 are preferably used in the process of the present invention. These are catalysts on inert supports with a BET surface area of less than 20 $m^2/g$, or $\alpha$-$Al_2O_3$ with a BET surface area of less than 10 $m^2/g$. The pretreatment with a base described in DE-OS 2 849 002 is not absolutely necessary, however.

Three classes of active substances are deposited on the support:

(a) 1-100 $g/l_{catalyst}$ of one or more metals from Groups 8 to 12 of the Periodic Table of Elements (here and below the designation of the Groups of the Periodic Table are as defined in the IUPAC recommendations of 1986), (b) 1-100 $g/l_{catalyst}$ of one or more transition metals from Groups 4 to 6 and 12 of the Periodic Table of Elements and (c) 1-100 $g/l_{catalyst}$ of one or more main group elements from Groups 14 and 15 of the Periodic Table of Elements.

Elements from Group 12 of the Periodic Table of Elements can thus act as active substances (a) and (b). Preferred active substances are Pd as metal (a), Ti, V, Nb, Ta, Cr, Mo, W as transition metal (b) and Pb and Bi as main group elements (c).

Most preferably, (a) 5-40 $g/l_{catalyst}$ of Pd, (b) 1-40 $g/l_{catalyst}$ in particular 5-40 g/l catalyst of V and (c) 2-20 $g/l_{catalyst}$ of Pb are applied to the support.

The active substances are preferably applied to the support in the form of their soluble salts, optionally several treatments (impregnations) are necessary for each component.

The contacts used in the process of the present invention are preferably operated in a temperature range between the inlet temperature of the reactant gas and a maximum of 600° C., preferably a maximum of 550° C., most preferably a maximum of 500° C.

Other preferred catalysts for use in the process of the present invention are those carrying Pd alone or with Rh and/or Ir and/or Ru on carbon supports having a low BET surface area. Such supports are graphite-containing or have graphite-like structures. Suitable are graphite itself, coke, such as needle coke or petroleum coke, and carbon nanotubes. These supports preferably have a BET surface area of from 0.2 to 10 $m^2/g$. Catalysts containing 0.001 to 1.5 mass % of Pd, based on the total mass of the catalyst, on graphite or graphite-containing coke or carbon nanotubes as the support in which up to 40% of the palladium can be replaced by Ir and/or Rh and/or Ru are preferably used. These catalysts therefore contain the precious metal(s) in the following arrangements on the support: Pd alone, Pd/Ir, Pd/Rh, Pd/Ru, Pd/Ir/Rh, Pd/Ir/Ru, Pd/Rh/Ru, or Pd/Ir/Rh/Ru. In many cases, one of the cited combinations of two or Pd alone is used. Palladium is preferably present in the catalysts on carbon supports in a quantity of 0.005 to 1 mass %, preferably 0.05 to 0.5 mass %, based on the total mass of the catalyst. If other metals from the so-called "platinum group" (Ru, Rh, Pd, Os, Ir, Pt) are used in addition to palladium, their proportion in total is preferably 10 to 40% based on the mass of palladium used; their mutual mass ratio is preferably 1:1 to 3:1 between any two.

It has also proven advantageous to dope the above-described catalysts additionally with a sulfur-containing or phosphorus-containing compound, preferably a phosphorus-containing compound. Such an additional content of doping agent is preferably from 0.1 to 2 mass %, preferably from 0.1 to 1 mass % of sulfur or phosphorus, preferably phosphorus, in chemically bound form, based on the total mass of the catalyst. Preferred examples of phosphorus-containing compounds for doping the catalysts useful in practicing the process of the present invention are: the oxo acids of phosphorus $H_3PO_4$, $H_3PO_3$, $H_3PO_2$ or their alkali salts, such as sodium dihydrogen phosphate, sodium or potassium phosphate or sodium hypophosphite.

The catalysts on carbon supports can be produced by applying the cited precious metals (Pd alone or with Rh and/or Ir and/or Ru) in the form of suitable salts along with the sulfur-containing or phosphorus-containing compound in separate operations, with drying after each application, onto one of the cited supports in the form of pellets, spheres, extruded granules or fragments measuring approximately 0.5 to 10 mm in size. Drying takes place in a known manner, for example at 100 to 140° C. and under a partial vacuum to normal pressure, for example, 1 to 1000 mbar. One example of a partial vacuum is that of a water jet pump. Aqueous solutions can be used to impregnate the support. This is preferably the case with the sulfur- or phosphorus-containing compounds, water-soluble examples of which are preferred. The precious metal salts can also be dissolved and applied in organic solvents such as simple alcohols, ketones, cyclic ethers or nitrites. Examples of such organic solvents are methanol, ethanol, propanol, isopropanol, acetone, methyl ethyl ketone, dioxane, acetonitrile and comparable solvents. In the case of salts with organic anions, methylene chloride and comparable solvents can also be used. Suitable precious metal salts are their chlorides, nitrates or acetates, for example.

After impregnation and subsequent drying, such a catalyst on carbon support can be used in the process of the present invention. However, it can also be activated before the start of hydrogenation of the nitroaromatic by a treatment with hydrogen at elevated temperature. Such an elevated temperature is in the range from 200 to 400° C., for example, preferably in the range from 200 to 380° C.

The catalysts on carbon supports are likewise operated in a temperature range up to a maximum of 600° C., preferably a maximum of 550° C., most preferably a maximum of 500° C.

In the event of a drop in activity, all of the catalysts described, regardless of the support and the type of active metal, can easily be regenerated in situ, i.e. in the hydrogenation reactor itself, with air or oxygen-containing gas mixtures. In the case of catalysts on carbon supports, such a regeneration is not possible if carbon supports other than those described are used, e.g. with activated carbon as a support, because activated carbon begins to burn if regenerated in such a way. A treatment with hydrogen at 200 to 400° C. can follow to reactivate the catalyst.

The contacts described as being preferred allow a particularly long cycle time in the process of the present invention.

In principle, the catalyst grains can have any shape, e.g., spheres, rods, Raschig rings, Pall rings or granules or tablets. The average particle size is typically between 100 and 5000 μm. Shaped bodies are preferably used whose beds have a low resistance to fluid flow and good gas/surface contact, such as Raschig rings, saddles, cart wheels and spirals.

In place of catalyst beds, suitable packing can also be used as the support. Examples include honeycomb bodies, monoliths or corrugated layers. For use in the process of the present invention, these packing types are naturally activated by the application of suitable metal compounds before being introduced into the reactor.

The load on the catalysts in the process of the present invention can be very high and can be from 0.1 to 20, preferably up to 15, more preferably up to 10 and most preferably up to 5 $g_{nitroarene}/[ml_{catalyst} \cdot h]$. Where multiple reactors are connected in series, the load can be varied from one reactor to another. However, the load in all reactors is preferably in the range from 0.1 to 20 $g_{nitroarene}/[ml_{catalyst} \cdot h]$. The process of the present invention is characterised accordingly by high space-time yields.

The fixed catalysts can be arranged in one reactor or in multiple reactors connected in series or operated in parallel. In the case of multiple catalyst beds connected in series, after the gas stream has passed through one catalyst bed, fresh nitroaromatic and hydrogen are preferably metered into the gas stream before the next catalyst bed to replace the consumed portions and optionally to establish a different nitroarene loading.

The evaporation of the nitroarene can take place as described in DE 1 809 711, but the nitroarene is preferably completely evaporated in fresh hydrogen and then introduced into the recycle gas stream in gaseous form. The advantage of this processing mode lies in the markedly lower formation of deposits in the reactor and in the feed lines. The evaporation can take place according to the prior art in known evaporators, such as falling-film, riser, injection, film, circulation and coil evaporators.

Atomization of the liquid nitroarene into the fresh hydrogen or recycle hydrogen stream by means of single-fluid or two-fluid nozzles is also possible. The reactant gas stream can be combined after superheating in a heat exchanger. The evaporation stage can be followed by a generally known droplet separation stage. The reactant gas stream is mixed in a known manner by means of appropriate feeding and distribution and/or by means of mixing devices in the circuit.

In one embodiment of the process of the present invention, an additional bed of inert material is added ahead of the heterogeneous catalyst in the direction of flow, the particle diameter in comparison to the catalyst itself being 1.5 to 100 times larger. This has the advantage that any droplets of the nitro compound used that were not evaporated during atomization can be separated off and evaporated further before they come into contact with the catalyst bed. The particles used for this purpose can optionally also be impregnated with an oxidation catalyst, preferably an oxide of vanadium.

After each catalyst bed, the reaction mixture leaving it is preferably cooled to the inlet temperature of the next reactor with vapor recovery (preferably water vapor). To this end, it is preferably passed through one or more heat exchangers. These can be any of the heat exchangers known to the person skilled in the art, such as shell-and-tube, plate, ring-shaped groove, spiral flow, or fin-tube heat exchangers.

After leaving the reactor or the last reactor in the direction of flow in the case of multiple reactors connected in series, the product gas is first used for superheating and production of vapor (preferably water vapor). Preferably only after this step is the gas mixture cooled sufficiently for aromatic amine to be removed from the gas mixture by condensation.

In a particularly cost-effective embodiment of the process of the present invention, the reaction water obtained in gaseous form is preferably condensed out only incompletely and the residual water vapor is recycled together with the remaining recycle gas so that no external addition of water is necessary.

In the process of the present invention, hydrogen is separated off from the reaction mixture obtained in the hydrogenation and the hydrogen, which is substantially free from the aromatic amine, is returned to the hydrogenation. The hydrogen is preferably separated by widespread condensation of the aromatic amine and at least partial condensation of water vapor. The gas stream obtained in this way, containing hydrogen and preferably also water vapor, is then returned to the hydrogenation, optionally after further processing steps. The recycled gas stream is preferably first replenished with fresh nitrobenzene and additional hydrogen and then returned to the hydrogenation.

The condensation condenses out the proportion of aromatic amine that can be condensed with reasonable technical effort and at reasonable expense. The proportion of aromatic amine returned to the hydrogenation with the hydrogen stream is therefore preferably less than 15%, more preferably less than 10%, even more preferably less than 10%, most preferably less than 5% of the aromatic amine obtained from the hydrogenation. Therefore, in the process of the present invention, a gas mixture which per mole preferably contains a maximum of 0.4 moles of amino groups in the form of the aromatic amine produced is passed through the fixed catalysts in the reactor or in the first reactor in the direction of flow in the case of multiple reactors connected in series. These small residual concentrations of recycled amine that may occur result from the fact that a complete separation of the product under the conditions that can be achieved in industry is generally not necessary and also not cost-effective.

The recycle gas stream then preferably passes through one or more compressors in order to balance out the flow resistance of reactors and heat exchangers and to control the mass flow of the recycle gas.

The compressors can be simple, known machines (e.g., liquid ring pumps, rotary piston blowers, turbo blowers or compressors) because the pressure loss can be kept low through the construction of the reactors. Dry-running compressors are preferably used.

The hydrogen removed from circulation, which is largely free from the aromatic amine, is fed back into the recycle gas stream (recycled) ahead of the reactor or of the first reactor in the direction of flow in the case of multiple reactors connected in series or of all reactors in the case of multiple reactors connected in parallel.

The condensate is transferred to a technical device for the separation of liquid phases and the aqueous and the organic phase are processed separately.

Aromatic amine recovered from the aqueous phase is sent to the processing stage for the organic phase. Processing is carried out in a known manner by distillation or by steam stripping.

The recycle gas is preferably heated back up to the inlet temperature of 150 to 400° C. immediately ahead of the reactor using a heat exchanger. Nitroaromatic compound and fresh hydrogen are metered in as described above before or afterwards, preferably afterwards.

The process of the present invention makes it possible to achieve a particularly long cycle time and exceptionally high selectivities with minimal recycle gas volumes. The reason for the long cycle time is the presence of water in the reaction gas. This delays the deactivation of the catalyst through coking. Water molecules compete successfully with organic molecules for the free centers on the catalyst surface causing the residence time of the organic molecules to fall and the deactivation process to slow down. The amount of water needed to achieve this result can be even less than that described in EP 0 696 573 B1.

The widespread avoidance of the recycling of the amine formed has considerable economic advantages, since large amounts of the valuable product do not have to be constantly recycled. For comparison, in EP 0 696 573 B1 the amount of amine returned ahead of the first fixed catalyst is at least five times higher than that in the present invention. In EP 0 696 573, a minimum of 2 moles of amino groups per mole of nitro group are returned as compared to the present invention in which a maximum of 0.4 moles of amino groups per mole of nitro group are returned. In principle, the recycling of amine can be avoided altogether in the present invention. It is only the technical and economic boundary conditions in large production plants which make a complete separation of the amine produced impracticable.

A particular increase in selectivity, especially in start-up processes, can easily be achieved by the addition of nitrogen, as can also be seen from the examples.

EXAMPLES

Example 1

Comparative Example

With No Water in the Reactant Stream

In the plant described below, a catalyst containing palladium (18 g/$l_{catalyst}$; corresponds to approx. 1.8 mass % palladium), vanadium (18 g/$l_{catalyst}$) and lead (6 g/$l_{catalyst}$) on an $\alpha$-$Al_2O_3$ support with an average particle diameter of 1.6 mm and a BET surface area of 5 $m^2$/g was used.

A mini-plant with three reactors connected in series was used as the test plant. The plant had no closed recycle gas system for hydrogen recycling. Nitrobenzene was pumped into the evaporators from above using metering pumps. In an analogous manner, recycled reaction water could be pumped into the evaporator using a metering pump. The hydrogen was fed into the evaporators which were heated with oil thermostats (approx. 250° C.), from below so that the nitrobenzene pumped in from above could evaporate countercurrently. The hydrogen supply was controlled ahead of the evaporators by means of mass flow controllers, the pressure in the plant was adjusted by means of a pressure regulating valve after the outlet.

The reactors were each made up of a stainless steel tube. A bed made from inert stainless steel coils and $\alpha$-$Al_2O_3$ was positioned on a screen. On these inert layers was placed the catalyst (particle diameter approx. 1.6 mm, 400 mm bed depth), followed by a further inert bed. In this way, a bed comprising approx. 130 ml of catalyst was obtained in each reactor. An inner pipe containing a height-adjustable thermocouple extended through each bed, allowing the axial temperature progression to be determined continuously.

After leaving the first reactor, the carrier gas was cooled to the desired inlet temperature for the second reactor using Marlotherm oil. After leaving the second reactor, the carrier gas was cooled to the desired inlet temperature for the third reactor using Marlotherm oil. No condensation of the reaction products took place between these reactors. After the third reactor, the reaction product was cooled with water, the non-volatile components were removed by condensation and separated from the gaseous components in a separator connected downstream.

The liquid components were transferred from the separator into the product collecting vessel and collected there (glass vessel). A liquid sample could be taken from this vessel which corresponded to an average value over an extended period (total condensate). The liquid samples were analyzed by gas chromatography.

With an average load of 1.2 $g_{nitroarene}$/[$ml_{catalyst}$·h] (first reactor) or 1.5 $g_{nitroarene}$/[$ml_{catalyst}$·h] (second and third reactors) and a hydrogen: nitrobenzene ratio of about 80:1, nitrobenzene-free aniline was produced for approximately 450 hours. Thereafter, the nitrobenzene content in the total condensate rose rapidly to 3500 ppm and the experiment was terminated.

Example 2

Example According to the Invention

The conditions recited in Example 1 were maintained and 2 moles of water per mole of nitrobenzene were additionally introduced into the first reactor. After 460 hours it could already be determined with certainty that the travel rate of the reaction zone through the first reactor was substantially slower than in Example 1. No signs of nitrobenzene leakage could be detected. The experiment was therefore interrupted in order to save time. By extrapolation it was determined that the addition of water more than doubled the cycle time to around 1100 hours.

Example 3

Example According to the Invention

The experiment was performed in a mini-plant which was constructed in a manner analogous to that used in Example 1 and was additionally fitted with a recycle gas compressor to recycle the gas streams.

In this plant, a catalyst which contained palladium (9 g/$l_{catalyst}$; corresponds to approx. 0.9 mass % palladium), vanadium (9 g/$l_{catalyst}$) and lead (3 g/$l_{catalyst}$) on an $\alpha$-$Al_2O_3$ support with an average particle diameter of 1.6 mm and a BET surface area of approx. 5 $m^2$/g was used. With an average total load of approx. 1.5 $g_{nitroarene}$/[$g_{catalyst}$·h], an average molar hydrogen:nitrobenzene ratio of approx. 90:1, a molar water:nitrobenzene ratio ahead of the first reactor of approx. 4:1 and a pressure which was increased successively from 3 to 5 $bar_{(abs)}$, a cycle time of 1500 hours could be obtained (termination criterion: the position of the reaction zone in all reactors is just before the end of the bed (but there are still no signs of nitrobenzene leakage in the total condensate)). The aniline average selectivity measured over the entire cycle was 99.7%.

Example 4

Example According to the Invention

Low Nitrogen Concentration

The conditions recited in Example 3 were maintained, with the exception of the pressure (in this case a constant 4 $bar_{(abs)}$) and the percentage molar ratio of hydrogen to nitrogen. This was adjusted to a value of approx. 90:10.

Example 5

Example According to the Invention

High Nitrogen Concentration

The conditions recited in Example 4 were maintained, with the exception of the percentage molar ratio of hydrogen to nitrogen; starting from approx. 50:50, this was raised successively to approx. 80:20 over 75 hours.

The experiments described in Examples 4 and 5 were terminated prematurely on basis of time, since only the influence of nitrogen concentration on start-up selectivity was to be investigated. It was established that a partial replacement of the hydrogen used hyperstoichiometrically with nitrogen had a considerable positive influence on the selectivity. Thus in Example 5, a selectivity of >99% was achieved after just 2 hours; this was the case in Example 4 after only 30 hours, and in Example 3 (with no nitrogen at all) after only 75 hours.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for producing aromatic amines represented by the formula

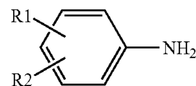

in which $R^1$ represents hydrogen, a methyl group, an ethyl group or an amino group, and $R^2$ represents hydrogen, a methyl group, or an ethyl group comprising hydrogenating a nitroaromatic compound represented by the formula

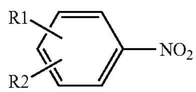

in which $R^2$ represents hydrogen, a methyl group, or an ethyl group, and $R^3$ represents hydrogen, a methyl group, an ethyl group, or a nitro group, with hydrogen on a fixed catalyst, in which:

(1) hydrogenation is performed at
  (a) an absolute pressure of from 1 to 50 bar,
  (b) a gas mixture inlet temperature of from 150 to 400° C., and
  (c) a maximum catalyst temperature of 600° C. under adiabatic conditions, and (2) a gas mixture comprising:
  (i) from 3 to 150 moles of hydrogen per mole of nitro groups and
  (ii) from 1 to 100 moles of water per mole of nitro groups is passed through the fixed catalyst at the start of hydrogenation, and (3) hydrogen which is substantially free from aromatic amine which is separated from the reaction mixture during hydrogenation is returned to the hydrogenation reaction.

2. The process of claim 1 in which the nitroaromatic compound is represented by the formula

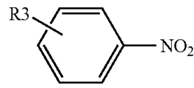

in which $R^3$ represents hydrogen, a methyl group, an ethyl group or a nitro group.

3. The process of claim 1 in which the hydrogenation is performed in 1 to 10 reactors connected in series.

4. The process of claim 3 in which one or more of the reactors connected in series is replaced by up to 5 reactors connected in parallel.

5. The process of claim 1 in which the hydrogenated reaction mixture is cooled and dissipated heat therefrom is used to generate steam.

6. The process of claim 3 in which nitroaromatic compound and hydrogen are fed into the gas mixture before that gas mixture is introduced into each reactor.

7. The process of claim 1 in which the fixed catalyst is in the form of a catalyst bed having a thickness of between 1 cm and 5 m.

8. The process of claim 1 in which the catalyst comprises:

(I) 1-100 $g/l_{catalyst}$ of one or more metals from Groups 8 to 12 of the Periodic Table of Elements, (II) 1-100 $g/l_{catalyst}$ of one or more transition metals from Groups 4 to 6 and 12 of the Periodic Table of Elements, and (III) 1-100 $g/l_{catalyst}$ of one or more main group elements from Groups 14 and 15 of the Periodic Table of Elements on a support with a BET surface area of less than 20 $m^2/g$.

9. The process of claim 8 in which the catalyst comprises: (I) from 5 to 40 g of Pd, (II) from 1 to 40 g of Ti, V, Nb, Ta, Cr, Mo and/or W and (III) from 2 to 20 g of Pb and/or Bi per liter of catalyst on $\alpha$-$Al_2O_3$.

10. The process of claim 1 in which the catalyst comprises palladium on a carbon support having a BET surface area of 0.2 to 10 $m^2/g$ and a palladium content of from 0.001 to 1.5 mass %, based on the total mass of the catalyst.

* * * * *